United States Patent
Balestra et al.

(10) Patent No.: US 6,756,398 B1
(45) Date of Patent: Jun. 29, 2004

(54) POSITIVE MODULATORS OF NICOTINIC RECEPTOR AGONISTS

(75) Inventors: Michael Balestra, Wilmington, DE (US); David Gurley, Wilmington, DE (US); James Rosamond, Wilmington, DE (US)

(73) Assignee: Astrazeneca AB, Sodertalje (SE)

(*) Notice: Subject to any disclaimer, the term of this patent is extended or adjusted under 35 U.S.C. 154(b) by 0 days.

(21) Appl. No.: 10/111,028

(22) PCT Filed: Nov. 1, 2000

(86) PCT No.: PCT/SE00/02149

§ 371 (c)(1),
(2), (4) Date: Apr. 18, 2002

(87) PCT Pub. No.: WO01/32620

PCT Pub. Date: May 10, 2001

(30) Foreign Application Priority Data

Nov. 3, 1999 (SE) .............................................. 9903996

(51) Int. Cl.[7] .................... C07D 209/08; A61K 31/404; A61P 25/00
(52) U.S. Cl. ........................................ 514/414; 548/451
(58) Field of Search ........................... 514/414; 548/451

(56) References Cited

FOREIGN PATENT DOCUMENTS

| WO | WO9626923 A1 | 9/1996 |
|---|---|---|
| WO | WO9964044 A1 | 12/1999 |

OTHER PUBLICATIONS

Goodman & Gilman's, The Pharmaceutical Basis of Therapeutics, 10th Edition, 2001, p. 549.*

J. Med. Chem., vol. 39, 1996, Serge Halazy et al, "Serotonin Dimers: Application of the Bivalent Ligand Approach to the Design of New Potent and Selective 5–HT1B/ID Agonists" p. 4920–p. 4927.

STN International, File CAPLUS, CAPLUS accession No. 1975:601816, Document No. 83:201816, Il'ina, G.N. et al: "Synthesis and pharmacological activity of 5,5'–acyldioxytryptamine"; Khim.–Farm. Zh. (1975), 9(7), 17–21.

* cited by examiner

Primary Examiner—Joseph K. McKane
Assistant Examiner—Kamal Saeed
(74) Attorney, Agent, or Firm—Kenneth F. Mitchell

(57) ABSTRACT

Compounds of Formula I

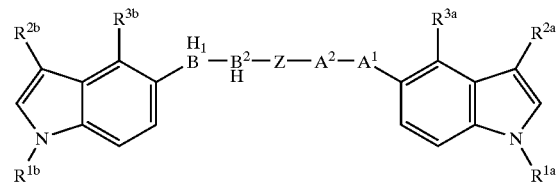

wherein $R^{1a}$, $R^{1b}$, $R^{2b}$, $R^{3b}$, $R^{3a}$, $R^{2a}$, $B^1$, $B^2$, Z, $A^2$ and $A^1$ are as defined in the specification, enantiomers thereof, pharmaceutically-acceptable salts thereof, processes for preparing them, pharmaceutical compositions containing them and their use in therapy, especially for treatment of conditions associated with reductions in nicotinic transmission. Compounds of the invention enhance the efficacy of agonists at nicotinic receptors.

9 Claims, No Drawings

POSITIVE MODULATORS OF NICOTINIC RECEPTOR AGONISTS

REFERENCE TO RELATED APPLICATIONS

This is a Section 371 filing of International Application No. PCT/SE00/02149 filed Nov. 1, 2000, pending, which claims priority under the Paris Convention to Application No. 9903996-8 filed in Sweden on Nov. 3, 1999.

The present invention relates to novel compounds or pharmaceutically acceptable salts thereof, processes for preparing them, pharmaceutical compositions containing them and their use in therapy. The novel compounds referred to are positive modulators of nicotinic receptor agonists, said positive modulator having the capability to increase the efficacy of the said nicotinic receptor agonists.

BACKGROUND

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits (for reviews, see Colquhon et al. (1997) Advances in Pharmacology 39, 191–220; Williams et al. (1994) Drug News & Perspectives 7, 205–223; Doherty et al. (1995) Annual reports in Medicinal Chemistry 30, 41–50). Members of the nAChR gene family have been divided into two groups based on their sequences; members of one group are considered β subunits, while a second group are classified as α subunits (for reviews, see Karlin & Akabas (1995) Neuron 15, 1231–1244; Sargent (1993) Annu. Rev. Neurosci. 16, 403–443). Three of the α subunits, α7, α8 and α9, form functional receptors when expressed alone and thus presumably form homooligorneric receptors.

An allosteric transition state model of the nAChR involves at least a resting state, an activated state and a "desensitized" closed channel state (Williams et al., supra; Karlin & Akabas, supra). Different nAChR ligands can thus differentially stabilize the conformational state to which they preferentially bind. For example, the agonists ACh and (−)-nicotine stabilize the active and desensitized states.

Changes of the activity of nicotinic receptors has been implicated in a number of diseases. Some of these, e.g. myasthenia gravis and ADNFLE (autosomal dominant nocturnal front lobe epilepsy) (Kuryatov et al. (1997) J. Neurosci. 17(23):9035–47), are associated with reductions in the activity of nicotinic transmission either through a decrease in receptor number or increased desensitization, a process by which receptors become insensitive to the agonist. Reductions in nicotinic receptors have also been hypothesized to mediate cognitive deficits seen in diseases such as Alzheimer's disease and schizophrenia (Williams et al., supra). The effects of nicotine from tobacco are also mediated by nicotinic receptors. Increased activity of nicotinic receptors may reduce the desire to smoke.

The use of compounds which bind nicotinic acetylcholine receptors in the treatment of a range of disorders involving reduced cholinergic function such as Alzheimer's disease, cognitive or attention disorders, attention deficit hyperactivity disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al., supra.

However, treatment with nicotinic receptor agonists which act at the same site as ACh is problematic because ACh not only activates, but also blocks receptor activity through processes which include desensitization (for a review, see Ochoa et al. (1989) Cellular and Molecular Neurobiology 9, 141–178) and uncompetitive blockade (open-channel block); Forman & Miller (1988) Biophysical Journal 54(1):149–58. Furthermore, prolonged activation appears to induce a long-lasting inactivation. Therefore agonists of ACh can be expected to reduce activity as well as enhance it. At nicotinic receptors in general, and, of particular note, at the α7-nicotinic receptor, desensitization limits the duration of current during agonist application.

Disclosure of the Invention

It has surprisingly been found that certain compounds can enhance the efficacy of agonists at nicotinic receptors. It is believed that compounds having this type of action (hereinafter referred to as "positive modulators") will be particularly useful for treatment of conditions associated with reductions in nicotinic transmission. In a therapeutic setting such compounds could restore normal interneuronal communication without affecting the temporal profile of activation. In addition, they would not produce long-term inactivation as prolonged application of agonist may.

According to the invention it has been found that compounds of Formula I:

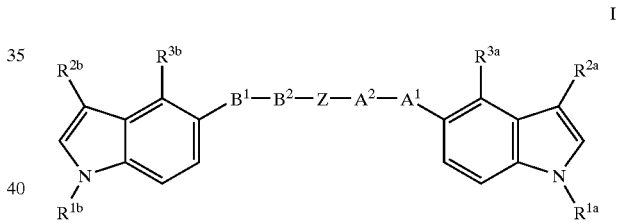

wherein, $R^{1a}$, $R^{1b}$, $R^{3a}$ and $R^{3b}$ independently represent hydrogen, or $C_1$–$C_4$ alkyl;

$R^{2a}$ and $R^{2b}$ independently represents hydrogen, $C_1$–$C_4$ alkyl, or $CH_2CN$;

$A^1$ represents oxygen, sulfur, or $NR^{4a}$;

$B^1$ represents oxygen, sulfur, or $NR^{4b}$;

$R^{4a}$ represents hydrogen, $C_1$–$C_4$ alkyl, $C_2$–$C_4$ alkenyl; or together $R^{3a}$ and $R^{4a}$ form a ring;

$R^{4b}$ represents hydrogen, $C_1$–$C_4$ alkyl, $C_2$–$C_4$ alkenyl; or together $R^{3b}$ and $R^{4b}$ form a ring;

$A^2$ and $B^2$ independently represent $C(O)$, $C(NH)$, $OC(O)$, $NHC(O)$, $NHC(S)$, $SO_2$, or a bond;

Z represents $(CH_2)_n Y (CH_2)_m$;

n and m are independently 0–4;

Y represents oxygen, sulfur, $NR^5$, $CHR^6$, Ar, or Ccy;

Ccy represents a 5–10 membered carbocycle including cyclopentane and adamantane;

Ar represents phenyl, naphthyl; or a 5- or 6-membered heterocyclic ring containing zero to four nitrogens, zero to one sulfurs and zero to one oxygens;

Ar is optionally substituted with one or more substituents selected from: hydrogen, halogen, $C_1$–$C_4$ alkyl, $C_2$–$C_4$ alkenyl, $C_2$–$C_4$ alkynyl, CN, $NO_2$, $CF_3$, $CR^7$, $NR^8R^9$, and $COOR^{10}$;

$R^7$, $R^8$ and $R^9$ are independently hydrogen, $C_1$–$C_4$ alkyl, aryl, heteroaryl, $C(O)R^{11}$, $C(O)R^{12}$, $SO_2R^{13}$, or, $R^8$ and $R^9$ together may be $(CH_2)_jQ(CH_2)_k$, where Q is oxygen, sulfur, $NR^{14}$, or a bond;

j is 2–4;

k is 0–2;

$R^5$, $R^6$, $R^{10}$, $R^{11}$, $R^{12}$, $R^{13}$ and $R^{14}$ are independently hydrogen, $C_1$–$C_4$ alkyl, aryl, or heteroaryl;

or an enantiomer thereof, and pharmaceutically acceptable salts thereof, enhance the efficacy of agonists at nicotinic receptors.

Preferred compounds of the invention include the following:

1,3-Bis(indolyl-5-oxymethyl)benzene;

N,N'-Di(5-indolyl)-1,3-adamantanedicarboxamide;

or an enantiomer thereof, and pharmaceutically acceptable salts thereof.

Unless otherwise indicated, the $C_1$–$C_4$ alkyl groups referred to herein, e.g., methyl, ethyl, n-propyl, n-butyl, i-propyl, i-butyl, t-butyl, s-butyl, may be straight-chained or branched, and the $C_3$–$C_4$ alkyl groups may also be cyclic, e.g., cyclopropyl, cyclobutyl.

Unless otherwise indicated, the $C_2$–$C_4$ alkenyl groups referred to herein may contain one or two double bonds, e.g., ethenyl, i-propenyl, n-butenyl, i-butenyl, allyl, 1,3-butadienyl. Unless otherwise indicated, the $C_2$–$C_4$ alkynyl groups referred to herein contain one triple bond, e.g., ethynyl, propynyl, 1-or 2-butynyl.

Halogen referred to herein may be fluoride, chloride, bromide, or iodide.

The compounds of the invention have the advantage that they may be less toxic, be more efficaous, be longer acting, have a broader range of activity, be more potent, produce fewer side effects, are more easily absorbed or have other useful pharmacological properties.

Methods of Preparation

In the reaction schemes and text that follow, $R^{1a}$, $R^{1b}$, $R^{2a}$, $R^{2b}$, $R^{3a}$, $R^{3b}$, $A^1$, $A^2$, $B^1$, $B^2$, and Z, unless otherwise indicated, are as defined above for formula I. The compounds of formula I may be prepared according to the methods outlined in Schemes I and II.

Compounds of formula I may be prepared from compounds of formula IIIa or IIIb, wherein $R^{1a}$, $R^{1b}$, $R^{2a}$, $R^{2b}$, $R^{3a}$, $R^{3b}$, $A^1$, $A^2$, $B^1$ and $B^2$ are as defined in formula I, by reaction with an intermediate of formula IIa or IIb, wherein $L^a$ or $L^b$ is a suitable leaving group representing halogen, triflate (TfO), methanesulfonate (MsO), or p-toluenesulfonate (pTsO) and $R^{1a}$, $R^{1b}$ $R^{2a}$, $R^{2b}$, $R^{3a}$, $R^{3b}$, $A^1$, $A^2$, $B^1$, $B^2$, and Z are as defined in formula I, in the presence of a suitable base and solvent. Intermediates of formula IIa or IIb may be prepared from compounds of formula IIIa or IIIb, wherein $R^{1a}$, $R^{1b}$, $R^{2a}$, $R^{2b}$, $R^{3a}$, $R^{3b}$, $A^1$, and $B^1$ are as defined in formula I, by selective reaction of one of the leaving groups of a compound of formula IV, wherein $L^a$ and $L^b$ are suitable leaving groups independently representing halogen, triflate (TfO), methanesulfonate (MsO), or p-toluenesulfonate (pTsO) and $A^2$, $B^2$ and Z are as defined in formula I, in the presence of a suitable base and solvent. Suitable bases include sodium carbonate ($Na_2CO_3$), cesium carbonate ($Cs_2CO_3$), potassium carbonate ($K_2CO_3$), triethylamine (TEA) or N,N-diisopropylethylamine (DIPEA). Suitable solvents for the reaction include N,N-dimethylformamide (DMF), N-methylpyrrolidone (NMP), acetonitrile (ACN), dimethylsulfoxide (DMSO) or tetrahydrofuran (THF). The reaction is preferably performed at a temperature of 0–100° C. and most preferably at ambient temperature.

Scheme I

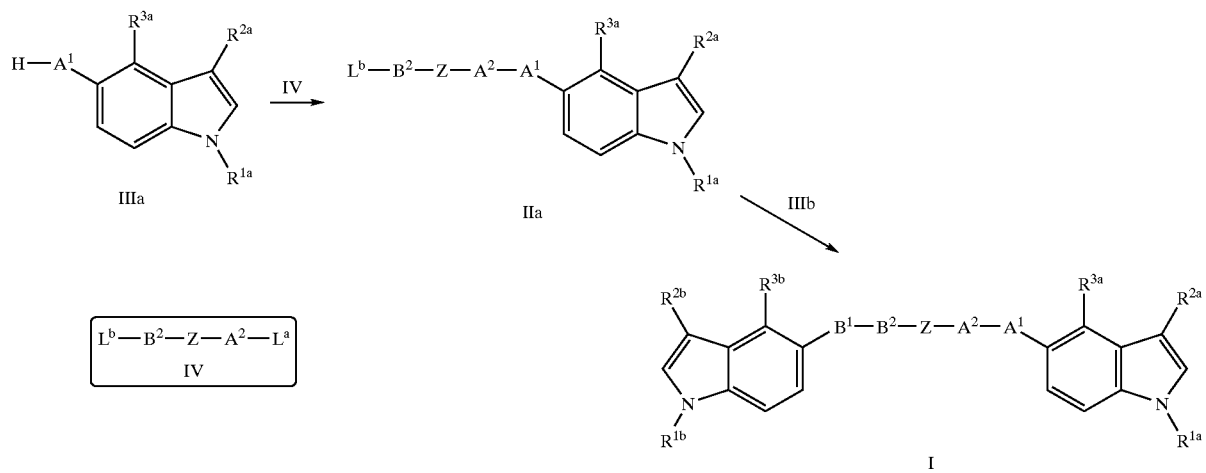

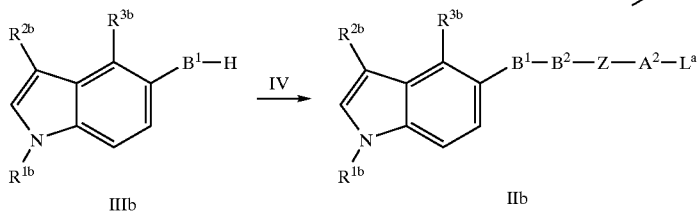

Intermediates of formula IIa or IIb may be prepared from compounds of formula IIIa or IIIb, wherein $R^{1a}$, $R^{1b}$, $R^{2a}$, $R^{2b}$, $R^{3a}$, $R^{3b}$, $A^1$ and $B^1$ are as defined in formula I, by condensation with a compound of formula IVa or IVb, wherein N=C=O is an isocyanate group and $L^a$ or $L^b$ are suitable leaving groups (or synthetic precursors) representing halogen, triflate (TfO), methanesulfonate (MsO), or p-toluenesulfonate (pTsO) and $A^2$, $B^2$, and Z are as defined in formula I, in the presence of a suitable solvent. Suitable solvents for the reaction include N,N-dimethylformamide (DMF), N-methylpyrrolidone (NMP), acetonitrile (ACN), dimethylsulfoxide (DMSO), tetrahydrofuran (THF), chloroform, ethyl acetate (EtOAc), ethanol (EtOH) or methanol (MeOH). The reaction is preferably performed at a temperature of 0–100° C. and most preferably at ambient temperature.

Compounds of formula IIIa and IIIb are either commercially available or may be prepared by methods known to one skilled in the art (see, for example, 'Indoles: Reactions and Synthesis' in 'Heterocyclic Chemistry', 3rd Edition, J. A. Joule, K. Mills, and G F. Smith, (Pub.) Stanley Thornes Ltd. (1998) and references therein).

Compounds of formula IIIa and IIIb, wherein $A^1$ represents $NR^{4a}$ where together $R^{3a}$ and $R^{4a}$ form a ring and/or wherein $B^1$ represents $NR^{4b}$ where together $R^{3b}$ and $R^{4b}$ form a ring, may be prepared by methods known to one skilled in the art (see, for example, J. E. Macor, J. T. Froman, R. J Post, K. Ryan, Tetrahedron Lett., 38, 1673–1676, 1997).

Compounds of formula IV, IVa and IVb are commercially available or may be prepared by methods known to one skilled in the art.

Where necessary, hydroxy, amino or other reactive groups may be protected using a protecting group as described in the standard text, 'Protecting Groups in Organic Synthesis', 3rd Edition, T. W. Greene and P. G. M. Wuts, 1999, J Wiley & Sons, Inc.

Scheme II

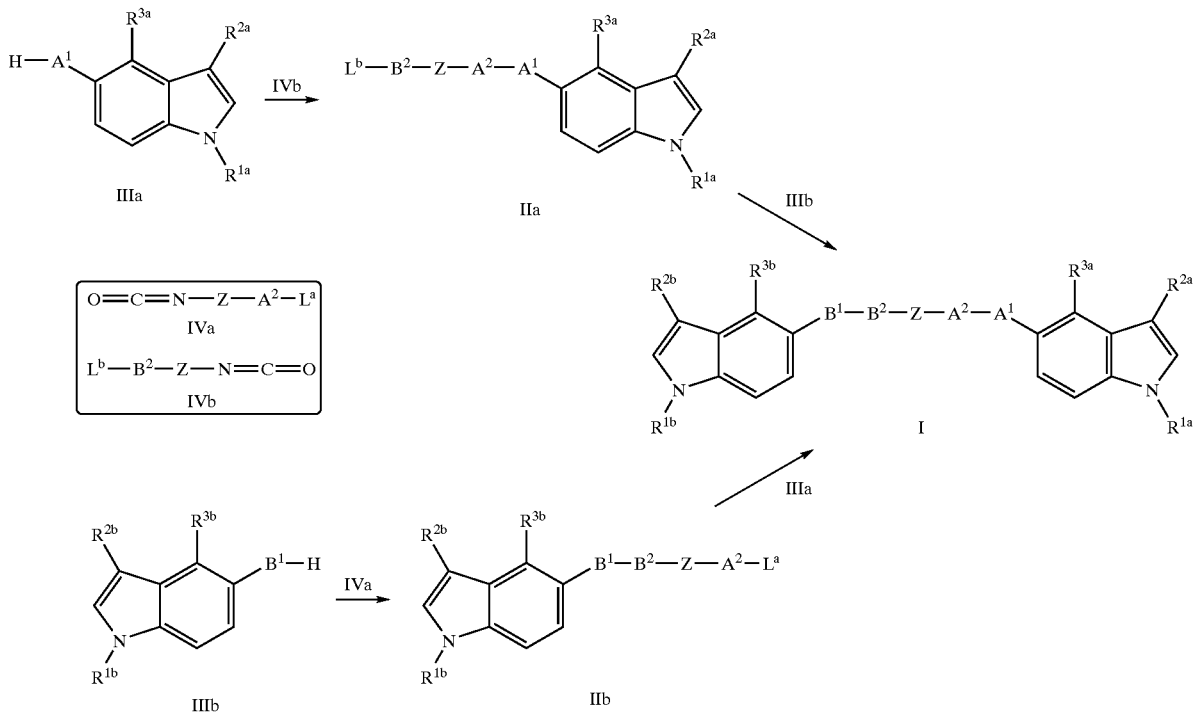

The above described reactions, unless otherwise noted, are usually conducted at a pressure of about one to about three atmospheres, preferably at ambient pressure (about one atmosphere). Unless otherwise stated, the above described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin. The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
  for tablets and dragees: lactose, starch, talc, stearic acid; for capsules: tartaric acid or lactose;
  for injectable solutions: water, alcohols, glycerin, vegetable oils; for suppositories: natural or hardened oils or waxes.

There is also provided a process for the preparation of such a pharmaceutical composition, which comprises mixing the ingredients.

It will be understood that a pharmaceutical composition comprising a positive modulator of a nicotinic receptor agonist together with a pharmaceutically acceptable carrier said positive modulator having the capability to increase the efficacy of the said receptor agonist. For the purposes of the present invention, the term "positive modulator" or "positive modulator of a nicotinic receptor agonist" shall be understood as a compound having the capability to increase the maximum efficacy of a nicotinic receptor agonist.

It will be understood that the invention includes compositions comprising either a positive modulator as the only active substance, thus modulating the activity of endogenous nicotinic receptor agonists such as acetylcholine or choline, or a positive modulator in combination with a nicotinic receptor agonist. Thus, the said pharmaceutical compositions containing a positive modulator of a nicotinic receptor agonist may, in addition comprise a nicotinic receptor agonist.

In a preferred form of the invention, the said nicotinic receptor agonist is an α7-nicotinic receptor agonist. Example of an α7-nicotinic receptor agonist is (−)-Spiro[1-Azabicyclo[2.2.2.]Octane-3,5*-Oxazolidine]-2*-One. Several α7-nicotinic receptor agonists are known in the art, e.g. from WO 96/06098, WO 97/30998 and WO 99/03859.

A further aspect of the invention provides a method for the treatment of a condition associated with reduced nicotine transmission, by administering to a patient in need of such treatment, a medically effective amount of a positive modulator of a nicotinic receptor agonist, said positive modulator having the capability to increase the efficacy of the said nicotinic receptor agonist.

It will be understood that the methods of treatment of this invention includes either a positive modulator as the only active substance, thus modulating the activity of endogenous nicotinic receptor agonists such as acetylcholine or choline, or a positive modulator administered together with a nicotinic receptor agonist.

In another preferred form of the invention, the said method of treatment includes a nicotinic receptor agonist, which is an α7-nicotinic receptor agonist. Example of an α7-nicotinic receptor agonist is (−)-Spiro[1-Azabicyclo [2.2.2.]Octane-3,5 *-Oxazolidine]-2*-One. Several α7-nicotinic receptor agonists are known in the art, e.g. from WO 96/06098. WO 97/30998 and WO 99/03859.

Utility

A further aspect of the invention is the use of compound according to the invention in the manufacture of a medicament for the treatment or prophylaxis of a condition associated with reduced nicotinic receptor transmission or a condition associated with reduced nicotinic density which could be one of the below mentioned diseases or conditions which comprises administering a therapeutically effective amount of compounds according to the invention to a patient.

It will be understood that the use includes compositions comprising either a positive modulator as the only active substance, thus modulating the activity of endogenous nicotinic receptor agonists such as acetylcholine or choline, or a positive modulator in combination with a nicotinic receptor agonist. Thus, the said use of pharmaceutical compositions containing a positive modulator of a nicotinic receptor agonist may, in addition comprise a nicotinic receptor agonist.

In a preferred form of the invention, the use of the said nicotinic receptor agonist is represented by an α7-nicotinic receptor agonist. Example of an α7-nicotinic receptor agonist is (−)-Spiro[1-Azabicyclo[2.2.2.]Octane-3,5*-Oxazolidine]-2*-One. Several α7-nicotinic receptor agonists are known in the art, e.g. from WO 96/06098, WO 97/30998 and WO 99/03859.

Examples of diseases or conditions include schizophrenia, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, jetlag, and nicotine addiction (including that resulting from exposure to products containing nicotine).

It will be understood that the said positive modulator can be administered either with the purpose of acting on endogenous nicotine receptor agonists such as acetylcholine or choline, or in combination with an exogenous nicotinic receptor agonist.

A further aspect of the invention relates to a compound for treating or preventing a condition or disorder as exemplified above arising from dysfunction of nicotinic acetylcholine receptor neurotransmission in a mammal, preferably a human, compositions comprising either a positive modulator as the only active substance, thus modulating the activity of endogenous nicotinic receptor agonists, or a positive modulator in combination with a nicotinic receptor agonist. Thus, the said use of pharmaceutical compositions containing a positive modulator of a nicotinic receptor agonist may, in addition comprise a nicotinic receptor agonist, effective in treating or preventing such disorder or condition and an inert pharmaceutically acceptable carrier.

Experimental Methods

The activity of the compounds of the invention may be measured in the tests set out below:

(a) Xenopus Oocyte Current Recording

The Xenopus oocyte has provided a powerful means of assessing the function of proteins thought to be subunits of ligand-gated ion-channels. Injection of RNA transcribed from cDNA clones encoding the appropriate receptor subunits, or injection of cDNA in which the coding sequence is placed downstream of a promoter, results in the appearance of functional ligand-gated ion-channels on the surface of the oocyte (see e.g. Boulter et al. (1987) Proc. Natl. Acad. Sci. U.S.A. 84, 7763–7767).

Consequently, one convenient technique to assess the enhancement of nicotinic efficacy is two-electrode voltage-clamp recording from Xenopus oocytes expressing $\alpha 7$-nicotinic receptors from cRNA.

$Xenopus\ laevis$ frogs (Xenopus I, Kalamazoo, Mich.) were anesthetized using 0.15% tricaine. Oocytes were removed to OR2 solution (82 mM NaCl, 2.5 mM KCl, 5 mM HEPES, 1.5 mM $NaH_2PO_4$, 1 mM $MgCl_2$, 0.1 mM EDTA; pH 7.4). The oocytes were defolliculated by incubation in 25 ml OR2 containing 0.2% collagenase 1A (Sigma) two times for 60 min on a platform vibrating at 1 Hz and stored in Leibovitz's L-15 medium (50 $\mu$g/ml gentomycin, 10 Units/ml penicillin, and 10 $\mu$g/ml streptomycin). Approximately 50 ng of cRNA was injected in each oocyte the following day. cRNA was synthesised from cDNA using Message Machine (purchased from Abion).

The external recording solution consisted of 90 mM NaCl, 1 mM KCl, 1 mM $MgCl_2$, 1 mM $BaCl_2$, 5 mM HEPES; pH 7.4. Two-electrode voltage-clamp recording was carried out using an Oocyte Clamp amplifier (OC 725C; Warner Instrument, Hamden, Conn.). Oocytes were impaled with two electrodes of 1–2 M$\Omega$ tip resistance when filled with 3M KCl. Recordings were begun when membrane potential became stable at potentials negative to −20 mV (resting membrane potentials are less negative when $Ba^{++}$ replaces $Ca^{-+}$ in bathing solutions). Membrane potential was clamped at −80 mV. ACh was purchased from Sigma. Oocytes were continuously perfused (5 ml/min) with recording solution with or without ACh.

Current amplitude was measured from baseline to peak. $EC_{50}$ values, maximal effect, and Hill slopes were estimated by fitting the data to the logistic equation using GraphPad Prism (GraphPad Software, Inc., San Diego, Calif.).

Increases in agonist efficacy elicited by a positive modulator can be calculated in two ways:

(1) As percent potentiation of current amplitude which is defined as $100(I_m-I_c)/I_c$ where $I_m$ is current amplitude in the presence of modulator and $I_c$ is current in the absence of modulator.

(2) As percent potentiation of "area under curve" of an agonist trace, which is the integration of net current over time. Area under the curve is a common representation of the total ion flux through the channel.

(b) $Ca^{2+}$ Flux Imaging

Imaging of $Ca^{2+}$ flux through nAChR $\alpha 7$ receptors transiently expressed in a cell line is another means of assaying modulator activity.

Cells expressing $\alpha 7$ receptors (for example HEK-293 cells or cell cultured neurons) are grown to confluence in 96 well plates and loaded with fluo-3, a fluorescent calcium indicator. To screen for $\alpha 7$ modulatory activity, the 96 well plate is placed in a fluorescence imaging plate reader (FLIPR) and test compounds along with an $\alpha 7$ agonist are applied simultaneously to all well. Receptor activation is measured by calcium influx into cells which is quantified by the increase in fluorescence intensity of each well, recorded simultaneously by the FLIPR. A modulatory effect is determined by the increase in fluorescence over that of agonist alone. Similarly, to test for nAChR $\alpha 7$ agonist activity, test compounds along with an $\alpha 7$ modulator are applied simultaneously to all wells. Receptor activation is measured by calcium influx into cells which is quantified by the increase in fluorescence intensity of each well, recorded simultaneously by the FLIPR. An agonist effect is determined by the increase in fluorescence over that of modulator alone. Cell-cultured neurons are prepared according to the following method: Eighteen day old Sprague-Dawley rat fetuses (E-18) were asceptically removed from the pregnant male, sacrificed, the frontal cortices of the brains removed, the menniges stripped, and the cleaned cortex placed into cold HBSS. If hippocampus was desired, the hippocampus was dissected away from the cortex and then placed into cold HBSS. The tissues were mechanically dispersed, washed once in HBSS (200 g for 30 minutes in 4° C.) resuspended in a modification of Sato's medium supplemented with glutamine, antibiotics, potassium chloride, insulin, transferrin, selenium, and 5% heat-inactivated fetal bovine serum (FBS; endotoxin free) and plated into each of a 24-well plate (coated with poly-L-lysine). The wells could contain glass coverslips which were also coated with PLL. The plates were incubated at 37° C. in a $CO_2$ incubator. After 24 hours the medium was removed, fresh medium added, and the cells allowed to grow for at least another 11 days, feeding when necessary.

The compounds of the invention are compounds, which causes a 100% potentiation (2-fold increase) of baseline current (as described above), as measured baseline to peak at low concentration of Acetylcholine (30 $\mu$M), indicating that they are expected to have useful therapeutic activity. The compounds of the invention are also compounds, which increase the flux of $Ca^{2+}$ when applied in the $Ca^{2+}$ flux-imaging assay, as described above. Any increase of $Ca^{2+}$ flux, caused by a compound of the invention, compared to the $Ca^{2+}$ flux caused by an agonist alone (as measured in Fluorescence Intensity Units) indicates that they are expected to have useful therapeutic activity.

The use of compounds of the invention have the advantage that they may be less toxic, be more efficacious, be longer acting, have a broader range of activity, be more potent, produce fewer side effects, are more easily absorbed or have other useful pharmacological properties.

General Experimental Procedures

Commercial reagents were used without further purification. Mass spectra were recorded following either chemical ionization (MS CI) or electrospray (MS ES) ionization methods and are reported as m/z for the protonated parent molecular ion ($MH^+$). Room temperature refers to 20–25° C.

EXAMPLES

The following examples are preferred non-limiting examples embodying preferred aspects of the invention.

Example 1

1,3-Bis(indolyl-5-oxymethyl)benzene

To a solution of 5-hydroxyindole (0.133 g) in N,N-dimethylformamide (20 ml) was added cesium carbonate (0.652 g) and α,α'-dibromo-m-xylene (0.132 g). The suspension was stirred under nitrogen at ambient temperature overnight. Cesium salts were removed by filtration and washed with acetone. The residue left on concentrating the combined filtrate and washings was chromatography over silica gel with a mixture of ethyl acetate and hexanes and precipitated from ether with hexanes to give 0.1 g of the title compound. MS CI (MH$^+$)=369.

Example 2

N,N'-Di(5-indolyl)-1,3-adamantanedicarboxamide

To a solution of 1,3-adamantanedicarboxylic acid (0.112 g) in chloroform (10 ml) at 0° C. was added thionyl chloride (0.18 g). The solution was allowed to warm to room temperature overnight and reduced to a residue at reduced pressure. The residue was dissolved in dry tetrahydrofuran and concentrated twice more to remove excess thionyl chloride. To a solution of the resulting acid chloride in tetrahydrofuran (20 ml) at 0° C. was added 5-aminoindole (0.13 g) and triethylamine (0.1 g) and the resulting suspension was allowed to warm to room temperature overnight. The precipitated triethylamine hydrochloride was removed by filtration and washed with tetrahydrofuran. The residue left on concentrating the combined filtrate and washings was chromatographed over silica gel with a mixture of ethyl acetate and hexanes to give 0.16 g of the title compound. MS ES (MH$^+$)=453.

What is claimed is:

1. A compound of Formula I:

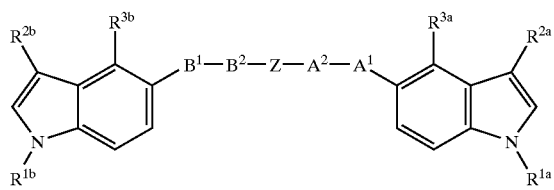

I wherein:

$R^{1a}$ and $R^{1b}$ represent hydrogen;

$R^{2a}$, $R^{2b}$, $R^{3a}$ and $R^{3b}$ independently represents hydrogen or $C_1$–$C_4$ alkyl;

$A^1$ represents oxygen or sulfur;

$B^1$ represents oxygen or sulfur;

$A^2$ and $B^2$ independently represent C(O), C(NH), OC(O), NHC(O), NHC(S), $SO_2$, or a bond;

Z represents $(CH_2)_n Y(CH_2)_m$;

n and m are independently 0, 1, 2, 3 or 4;

Y represents Ar, or Ccy;

Ccy represents cyclopentyl or adamantyl;

Ar represents phenyl or naphthyl;

Ar is optionally substituted with one or more substituents selected from: hydrogen, halogen, $C_1$–$C_4$ alkyl, $C_2$–$C_4$ alkenyl, $C_2$–$C_4$ alkynyl, CN or $CF_3$; or an enantiomer thereof, or a pharmaceutically-acceptable salt thereof.

2. A compound according to claim 1, said compound being:

1,3-Bis(indolyl-5-oxymethyl)benzene;

N,N'-Di(5-indolyl)-1,3-adamantanedicarboxamide; or an enantiomer thereof, or a pharmaceutically-acceptable salt thereof.

3. A method for the treatment of Alzheimer's disease, learning deficit, cognition deficit, attention deficit, memory loss, Attention Deficit Hyperactivity Disorder, Lewy Body Dementia, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, pain, or ulcerative colitis, comprising administering to a subject suffering therefrom a therapeutically-effective amount of a compound according to claim 1.

4. A pharmaceutical composition comprising a compound according to claim 1, in admixture with a pharmaceutically-acceptable diluent or carrier.

5. The pharmaceutical composition according to claim 4, for the use in the treatment of human diseases or conditions in which said composition has the capability to increase the efficacy of a nicotinic, wherein said disease or condition is selected from the group consisting of:

Alzheimer's disease, learning deficit, cognition deficit, attention deficit, memory loss, Attention Deficit Hyperactivity Disorder, Lewy Body Dementia, anxiety, schizophrenia, or mania or manic depression, Parkinson's disease, Huntington's disease, Tourette's syndrome, neurodegenerative disorders in which there is loss of cholinergic synapse, jet lag, cessation of smoking, nicotine addiction including that resulting from exposure to products containing nicotine, pain, or ulcerative colitis.

6. A method for the treatment of Alzheimer's disease, learning deficit, cognition deficit, attention deficit, memory loss, Attention Deficit Hyperactivity Disorder, Lewy Body Dementia, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, pain, or ulcerative colitis, comprising administering to a subject suffering therefrom a therapeutically-effective amount of the pharmaceutical composition according to claim 4.

7. A method of treatment of psychotic disorders or intellectual impairment disorders, in which activation of the α7 nicotinic receptor is beneficial which comprises administering a therapeutically effective amount of a compound according to claim 1.

8. The method according to claim 7, wherein the disorder is Alzheimer's disease, learning deficit, cognition deficit, attention deficit, memory loss, Attention Deficit Hyperactivity Disorder, Lewy Body Dementia, anxiety, schizophrenia, mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, pain, or ulcerative colitis.

9. The method according to claim 8, wherein the disorder is Alzheimer's disease.

* * * * *